(12) United States Patent  (10) Patent No.: US 7,175,434 B2
Brajnovic  (45) Date of Patent: Feb. 13, 2007

(54) IMPLANT ARRANGEMENT AND DEVICE

(75) Inventor: Izidor Brajnovic, Gothenburg (SE)

(73) Assignee: Nobel Biocare AB (publ.) (SE)

( * ) Notice: Subject to any disclaimer, the term of this patent is extended or adjusted under 35 U.S.C. 154(b) by 14 days.

(21) Appl. No.: 10/500,031

(22) PCT Filed: Dec. 19, 2002

(86) PCT No.: PCT/SE02/02387

§ 371 (c)(1),
(2), (4) Date: Jun. 24, 2004

(87) PCT Pub. No.: WO03/061512

PCT Pub. Date: Jul. 31, 2003

(65) Prior Publication Data

US 2005/0202370 A1  Sep. 15, 2005

(30) Foreign Application Priority Data

Dec. 28, 2001 (SE) .................... 0104432

(51) Int. Cl.
A61C 8/00 (2006.01)
(52) U.S. Cl. ...................... 433/174; 433/173
(58) Field of Classification Search ............. 433/172, 433/173, 181, 199.1
See application file for complete search history.

(56) References Cited

U.S. PATENT DOCUMENTS 5,015,186 A * 5/1991 Detsch ..................... 433/173
5,302,125 A * 4/1994 Kownacki et al. ........... 433/172
5,328,371 A  7/1994 Hund et al.
5,417,569 A  5/1995 Perisse
5,516,288 A * 5/1996 Sichler et al. .............. 433/173
5,704,936 A * 1/1998 Mazel ....................... 606/61
5,885,078 A * 3/1999 Cagna et al. .............. 433/172
6,190,169 B1 * 2/2001 Bluemli et al. ............ 433/172
6,902,401 B2 * 6/2005 Jorneus et al. ............. 433/173
6,942,699 B2 * 9/2005 Stone et al. ............. 623/19.14
2004/0063062 A1 * 4/2004 Brajnovic .................... 433/75

* cited by examiner

Primary Examiner—Ralph A. Lewis
(74) Attorney, Agent, or Firm—Connolly Bove Lodge & Hutz LLP

(57) ABSTRACT

In an arrangement with implant and attachment part/dental bridge, the latter comprises one or more recessed walls. The implant is designed or can cooperate with a portion which can be arranged on a spacer sleeve belonging to the implant and extends substantially parallel to the recessed wall. The attachment part and its respective recessed wall is arranged with displaceability in the main longitudinal direction of the implant relative to the outer surface of the portion. The portion is arranged to be expandable so that, in a given position of longitudinal displacement, it is possible to achieve interaction between outer surfaces of the portion and the recessed wall and thus anchoring of the attachment part to the portion or the implant. The invention also relates to a device with two or more implants and dental bridge. By means of the invention, discrepancies between dental bridge and the implants can be taken up in an effective and rapid securing principle.

12 Claims, 3 Drawing Sheets

FIG. 1
(CONVENTIONAL)
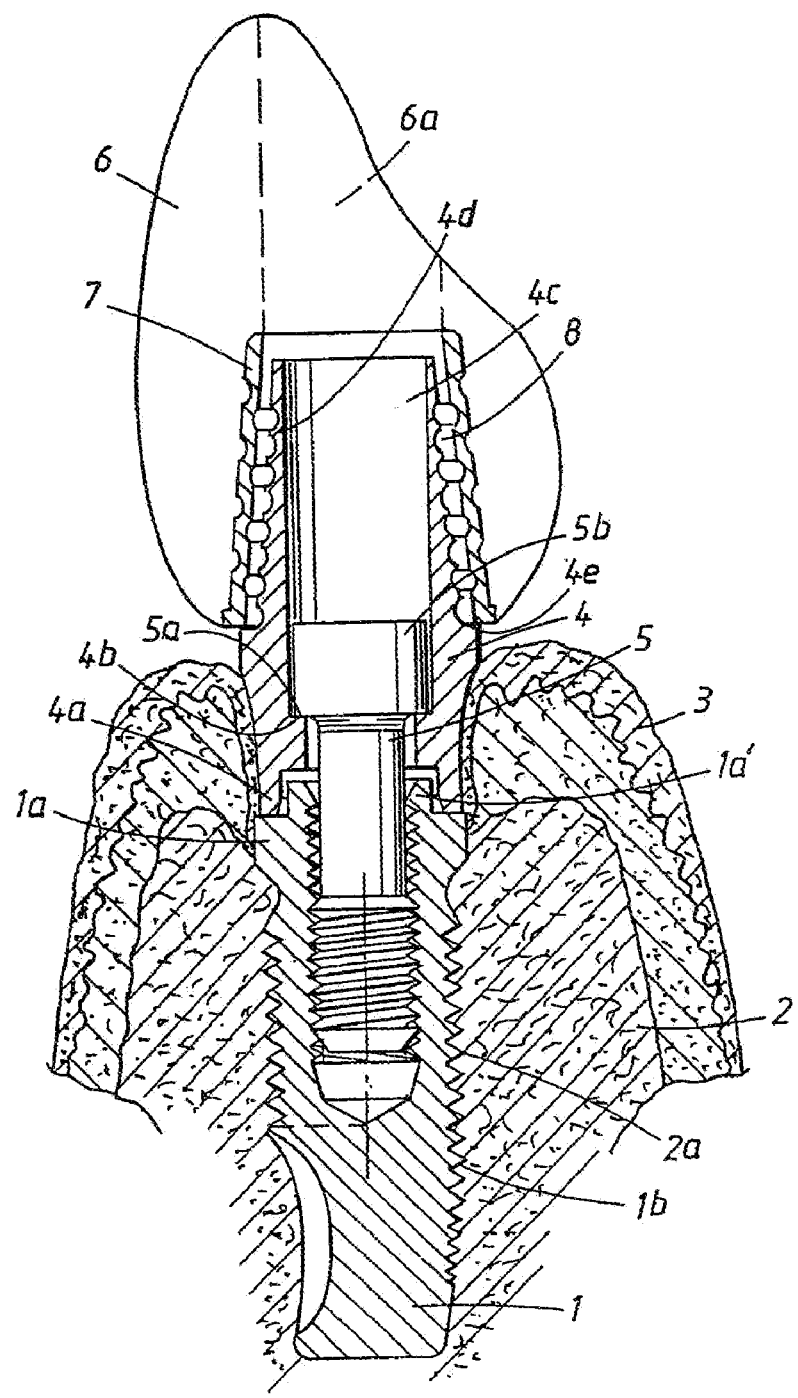

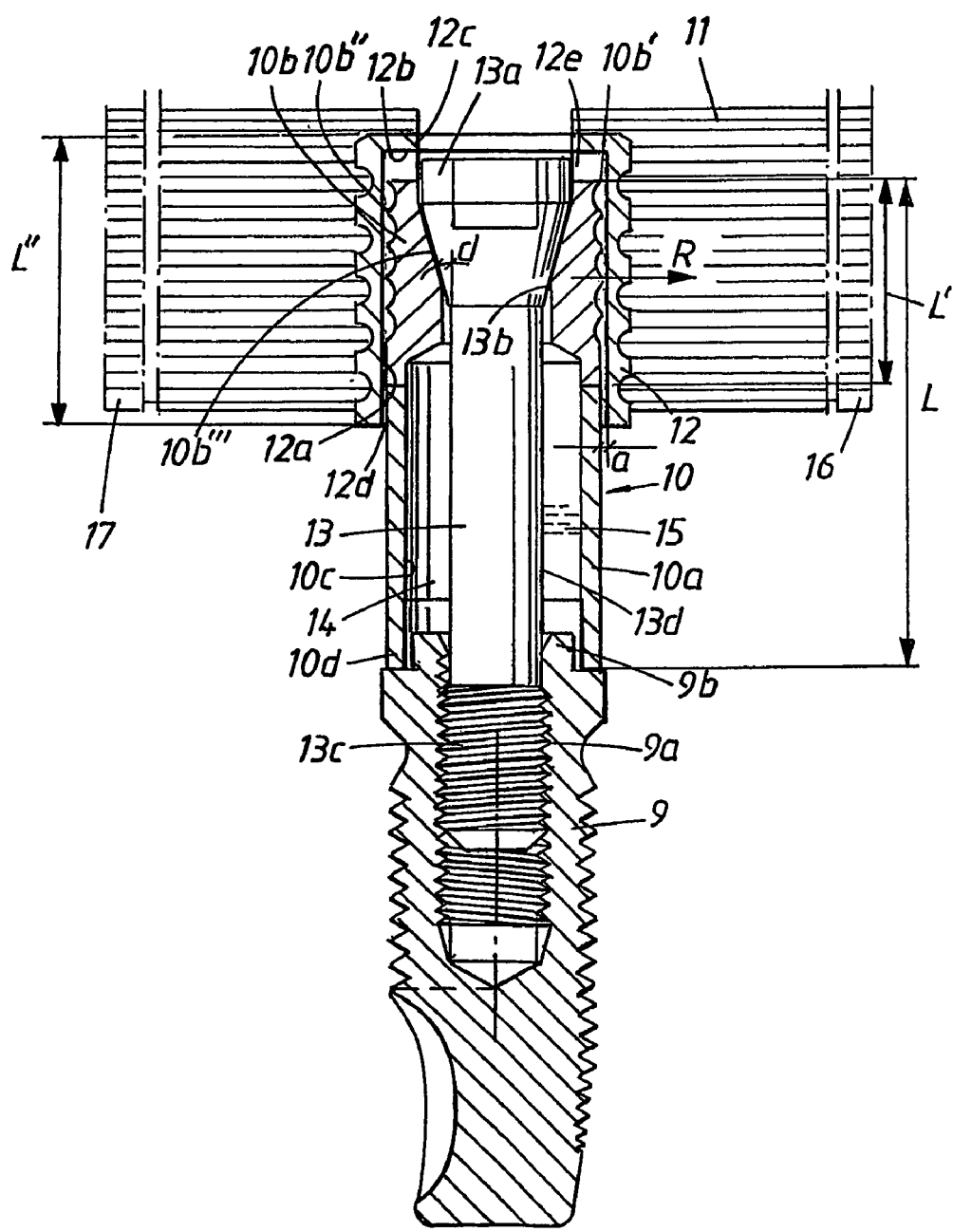

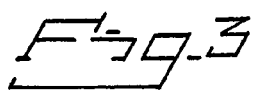
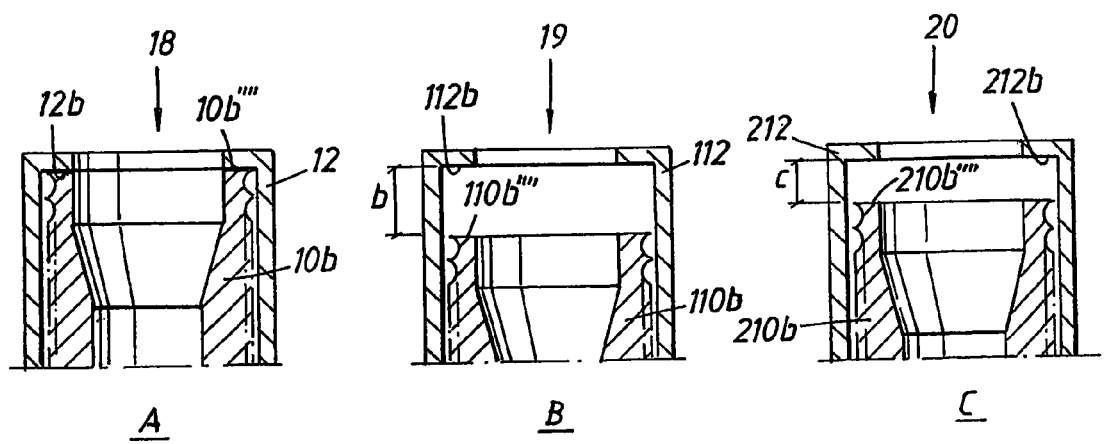
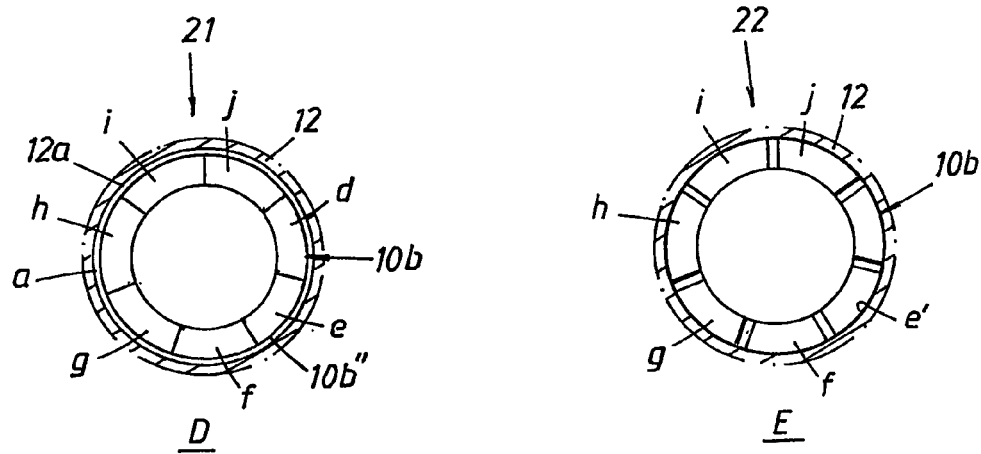

IMPLANT ARRANGEMENT AND DEVICE

BACKGROUND OF THE INVENTION

The present invention relates to an arrangement with implant and attachment part, for example in the form of a dental bridge. The attachment part comprises a recessed wall and the implant is designed or can cooperate with a portion which preferably can be applied on a spacer sleeve belonging to the implant. Said portion preferably extends substantially parallel to the recessed wall.

The invention also relates to a device with two or more implants and an attachment part which can cooperate with these and which in accordance with the above can have the form of a bridge. The attachment part comprises recesses for application to the implants via portions arranged on or applied to these and intended to extend into the recesses.

In production by means of modeling of bridges or the like for implants in jaw bone, there is always play between the concrete installation situation and the product finally produced, for example the bridge. The principle of securing the bridge or the like to the implant or to components belonging thereto (for example spacer sleeve or spacer sleeves) must take account of the play which is present. In accordance with attached FIG. 1, it is already known, in connection with attachment parts in the form of bridges, to use on the one hand recesses in the attachment part and on the other hand spacer sleeves which are arranged on the implant or the implants which are applied to the jaw bone, for example. The actual anchoring of the respective bridge on the spacer sleeve or the spacer sleeves can take place with the aid of cement which is applied between internal and external surfaces, designed as truncated cones or otherwise, of the respective bridge sleeve and spacer, while at the same time play is present between the components for taking up discrepancies.

The disadvantage of using cement or cement-like agents is considerable. Thus, for example, problems may arise in using the right amount of cement or equivalent. Too little cement may compromise the result, and too much cement means that excess cement occurs at the implant site. Problems may also arise relating to the hardening of the cement. Most cements have a very rapid hardening profile. It is also difficult, during the hardening process, to achieve exact and permanent positions for the respective bridge. Various types of cement (for example acryl-containing cement) are considered difficult to handle from the point of view of soiling. If there is no time to apply the dental bridge to the implants before the cement has hardened, it may also be difficult to make readjustments of the bridge position, since the cement connection then has to be broken up. Contamination may also arise on the jaw bone and gingiva (gum) when working with cement.

There is therefore a need for new securing principles when applying dental bridges to implants. The new securing principles must be able to function rapidly and safely and the adjustment work must be easy to carry out. The object of the present invention is to solve all or some of the set of problems specified above. It is also important to be able to use compatible material types so that safe and long-lasting fittings can be obtained. The invention also solves this problem.

SUMMARY OF THE INVENTION

The feature which can principally be regarded as characterizing the arrangement discussed in the introduction is that the attachment part and its recessed wall are arranged with displaceability in the main longitudinal direction of the implant relative to the outer surface of the portion, and in that the portion is arranged to be expandable so that, in a given position of longitudinal displacement, it is possible to achieve interaction between the outer surface of the portion and the recessed wall and thus anchoring of the attachment part to the portion, i.e. the implant.

In one embodiment, said portion is substantially cylinder-shaped and, at its front end, has mutually adjacent parts which, during the expansion, can be pressed outward in the radial direction. The parts extending adjacent to one another can be arranged with internal cone-shaped surfaces which combine to form an internal and thus truncated cone-shaped inner surface. The parts in question are arranged to be expandable by means of a fastening screw which is used, for example, for anchoring a spacer sleeve or equivalent. The fastening screw can be provided with a truncated cone-shaped outer surface which can cooperate with said inner surface, which permits a radial expansion, dependent on the position of insertion of the screw in the implant, for the parts extending adjacent to one another. In one embodiment, said recessed wall is arranged in a bridge sleeve which is applied on a given dental bridge. Alternatively, the dental bridge can be provided with a recess in its material, in which case the recessed wall is arranged in one such recess. The spacer sleeve can be made of hard titanium and the bridge sleeve can be made of soft titanium. The parts extending adjacent to one another on the spacer sleeve must be arranged in the recess so that they extend into the latter by at least ⅔ of their lengths. Further characteristics of said developments are set out in the attached dependent claims concerning the novel arrangement according to claim 1.

A device according to the invention can be considered to be characterized by the fact that each recess is arranged to be displaceable in the longitudinal direction of the respective implant relative to the respective portion, and that, upon anchoring of the attachment part to the portions or the implants, the longitudinal displacement position of the attachment part in relation to the portions/implants can be determined by means of the relative longitudinal displacement position, for example an end-position of longitudinal displacement, between one of the recesses and the portion/implant cooperating therewith. Further characteristics are that the positions arising between other recesses and portions form anchoring positions without length displacement-determining function for the dental bridge as such. Finally, the invention is characterized by the fact that said portions are arranged to be expandable so as to obtain, in said longitudinal displacement positions, cooperation between outer surfaces of the portions and the recessed walls and thus multi-point anchoring of the attachment part to the dental bridge.

In further developments of the novel device, a case is used in which the portions are located on spacer sleeves applied on the implants. Said parts on the spacer sleeve arranged adjacent to one another are expandable in substantially the radial directions. The inner recesses of the spacer sleeves and/or the inner spaces of the bridge sleeve constitute storage spaces for thixotropic and bactericidal agent, which can consist, for example, of hyaluronic acid.

By means of what is proposed above, a patient-friendly securing principle for dental bridges in implants is obtained which is rapid and effective and, inter alia, permits easy readjustment and exchange of the respective attachment part/dental bridge. Material types which have proven themselves in this context can be used in the bridge and spacer sleeve constructions and in the fastening screws. The application function is considerably simplified and can for example be controlled by end-position indication or end-position stops in one of the bridge's recesses. When the end position has been reached, the bridge is screwed tightly in place and at the same time acquires its "horizontal position" in the patient's mouth. Other longitudnal displacement positions between recesses and portions on other implants are determined by the initial fitting, and anchoring or anchorings can also be carried out in these longitudinal displacement positions.

BRIEF DESCRIPTION OF THE DRAWINGS

A presently proposed arrangement and proposed device will be described below with reference to the attached drawings, in which FIG. 1 shows the prior art by indicating an implant, shown in longitudinal section, anchored in a jaw bone and provided with a spacer sleeve, to or on which an attachment part has been applied, FIG. 2 shows the novel arrangement in longitudinal section on an implant arranged in a corresponding way in a jaw bone with applied spacer sleeve, to which a dental bridge has been screwed with a fastening screw, FIG. 3 shows, in longitudinal section, three bridge sleeves in a dental bridge which are applied on upper portions of spacer sleeves according to FIG. 2, the relative anchoring positions between the sleeves and the portions being arranged at different levels in the height directions of the implants, and FIG. 4 shows, in two different end views, the design of the upper or front parts of the spacer sleeve, one end view showing the parts in the unexpanded position and the second end view showing the parts in the expanded position.

DETAILED DESCRIPTION OF THE INVENTION

In FIG. 1, an implant is indicated by 1. The implant is screwed tightly in a jaw bone 2. The application of the implant can alternatively take place in another type of bone in the human body. The gum parts (gingiva) 3 of the jaw bone or equivalent have been exposed or opened at the implant site and have been shown in the folded back position. At its upper parts 1a, the implant can cooperate with or is provided with a spacer sleeve 4 which is anchored to the upper parts of the implant at an upwardly projecting flange or hexagon 1a' on the implant. The spacer sleeve has at the bottom a circular part 4a which surrounds the upwardly projecting part 1a'. In a manner known per se, the sleeve is also provided with an internal flange 4b which constitutes a support for a fastening screw, whose bottom surface 5a can cooperate with the internal flange in order to permit anchoring of the spacer sleeve in the implant by means of the fastening screw 5. The spacer sleeve is provided with an upper internal recess 4c for the head 5b of the screw 5. An attachment part 6 is applied on the spacer sleeve, at upper portions 4d of the latter. The attachment part is applied via a bridge sleeve which has been indicated by 7. The attachment part is also provided with a recess 6a, via which the fastening screw can be applied to the recess 4c in the spacer sleeve in order to allow the latter to be screwed tightly in the implant. In a manner known per se, the implant is provided with threads 1b, by means of which the implant can be screwed in a recess or a hole 2a in the dentine. At the bottom, the bridge sleeve 7 bears against an external flange 4e on the spacer sleeve so that an end position is obtained for the bridge sleeve in relation to the spacer sleeve. The bridge sleeve and the spacer sleeve are anchored to one another via a gap 8 which in accordance with a known technique is filled with cement in order to allow the attachment part to be affixed to the implant. In this connection, reference is made to the above and to the prior art.

The implant according to FIG. 2 can have a structure corresponding to that of the implant shown in FIG. 1, and the implant can be anchored to dentine in a corresponding way as has been shown for the implant according to FIG. 1. In FIG. 2, the implant is indicated by 9, the spacer sleeve by 10, a dental bridge by 11, a bridge sleeve arranged in the dental bridge by 12, and a fastening screw by 13. The dental bridge can be a dental bridge made of carbon fiber material. However, the invention can also be used for other types of bridge material and, in one embodiment, the bridge sleeve 12 can be replaced by a recess which is arranged directly in the bridge material. The spacer sleeve 10 which is cylindrical has in principle two parts, of which the first part has been indicated by 10a and the second part by 10b. The first part 10a consists of a substantially cylindrical part with full cylinder wall. The second part 10b is designed with or comprises a number of parts extending adjacent to one another (see also FIG. 4 below). A recessed wall in the bridge part 12 is shown by 12a. At the top, the bridge sleeve is provided with an internal flange 12b and the bridge sleeve is also arranged with a recess 12c at its upper part. The fastening screw can be applied to the spacer sleeve and the implant via said recess 12c. At the bottom too, the bridge sleeve is provided with a recess 12d so that the bridge sleeve can be engaged over the portion 10b of the spacer sleeve and so that the portion 10b extends into the space 12e of the bridge sleeve. The total length of the spacer sleeve is indicated by L, and the length of the portion or parts 10b is indicated by L'. The value or order of L' is approximately half or slightly less than half of the value or order of the length L. The height of the bridge sleeve is indicated by L" and a feature of the present embodiment is inter alia that the portion 10b must extend into the recess 12e by at least ⅔ of its length L'. The outer surface 10b' of the portions is arranged with irregularities or spikes 10b". The portion 10b" or its parts is/are arranged with inner surfaces 10b'" which are designed as parts of truncated cones, which inner surfaces combine to form an internal inner surface designed as a truncated cone. The head 13a of the screw 13 is provided with an external outer surface 13b which is designed as a truncated cone and which can be applied against said internal inner surfaces 10b'". Half the cone angle of said cone-shaped surfaces is indicated by α and can assume values of around 40°. The material of the spacer sleeve can be hard titanium, for example MGA 007, and the material of the bridge sleeve 12 can be soft titanium, for example MGA 002. The fastening screw 13 is made of gold. In accordance with the concept of the invention, the parts in portion 10b can be expanded with the aid of the fastening screw 13 when the latter is screwed into the implant via its threaded end 13c which cooperates with an internal thread 9a in the implant. The expansion takes place via the truncated cone-shaped inner and outer surfaces of the portion 10b and the screw 13/head 13a of the screw. Depending on the degree of screwing of the screw in the internal thread 9a of the implant, it is possible to achieve an expansion of such an order which brings about cooperation between the outer surface 10b' of parts of the portion 10b and the inner surface 12a. The different types of material and the angle α are chosen so that a residual expansion function exists in the screwed-in position of the screw 13. The cone-shaped surfaces mean that a residual wedging function can exist. In a gap-shaped space 14 between the inner surface 10c of the spacer sleeve and the outer surface 13d of the screw, a thixotropic material in the form of hyaluronic acid is introduced during or before the anchoring. Said agent can also be applied to or in the internal recess 12e of the bridge sleeve. The upwardly projecting flange of the implant can consist of a hexagon-shaped part which can be included in a function controlling the angle of rotation relative to the implant for the spacer sleeve which surrounds the part 9b with a lower part 10d.

In FIG. 2, the device for anchoring the dental bridge 11 to implants has been shown for one implant. The dental bridge or equivalent can normally be anchored to two or more implants, and in FIG. 2 the positions of two further implants have been indicated by 16 and 17. The other implants have a structure corresponding to the implant shown in FIG. 2, and this also applies to other components in the overall, construction. One difference may be that the portion 10b extends into the bridge sleeves by a different length because of the fact that there may be different positions for the longitudinal displacement of the different implants. A gap a is arranged in FIG. 2. This gap takes up any discrepancies in the radial direction between the different anchoring points. In accordance with the present invention, the parts, which form the portion 10b must be able to be expanded in the radial direction R so that the gap a in question is taken up with the aid of the anchoring function. The device is such that a considerable radial displacement is obtained for the entire outer surface or outer surfaces of the portion 10b or its parts arranged adjacent to one another. This is intended to obtain a cooperation between the outer surfaces 10b' of the parts and the inner surface 12a along substantial parts of the parts or along the length or height of the portion 10b. It is also important that the gap a is chosen so that the limit of elasticity is not exceeded or so that breaks do not occur in the parts of portion 10b which are arranged adjacent to one another. In the illustrative embodiment shown in FIG. 2, the gap a is chosen at ca. 3/10 mm and can be chosen in the range of 2/10 and 4/10 mm. These chosen values give a guarantee of a proper anchoring function.

FIG. 3 shows the mutual height positions between the portion 10b and the bridge sleeve 12. In this case, said positions of three different anchoring points 18, 19 and 20 are assumed or shown. In the anchoring point 18 according to the view A, the portion 12 has been inserted to the maximum extent into the bridge sleeve 12 so that the end surface 10b'''' of the portion 10b bears against the internal surface 12b of the bridge sleeve. At the anchoring point 9 according to the view B, there is another degree of insertion of the portion 110b in the bridge sleeve 112, so that the end surface 110b'''' is located at a distance b from the inner surface 112b. In the anchoring point 20 according to the view C, there is yet another degree of insertion of the portion 210b in the bridge sleeve 212 so that the end surface 210b'''' lies at a distance c from the inner surface 212b. From this it will be seen that any discrepancies which exist between the implants in their height directions can be taken up by the above-described anchoring principle. The anchoring principle also has a second function as regards the method of securing the dental bridge to the implants. The dental bridge can in fact first be applied to the implants until contact is made between the end surface 10b'''' and the inner surface 12b at one of the anchoring points where the anchoring by means of the expansion can be effected. The dental bridge has assumed the desired horizontal position in the patient's mouth. Thereafter, the anchoring can be effected at the other anchoring points without further adjustments in the height direction, i.e. the expansion can take place in the other anchoring points without having to take into account the height positions at these points. There is therefore an automatic height adjustment function for said other point or points when carrying out the anchoring in the first anchoring point.

FIG. 4 is intended to show the expansion function for the parts of the portion 10b which are arranged adjacent to one another, which parts have been indicated by d, e, f, g, h, i, j. In the function position 21 according to the view D, the parts assume unexpanded positions and the gap a' is thus present between the outer surface (the combined surface) 10b'' and the inner surface 12a of the bridge sleeve 12. In the function stage 22 according to the view E, the expansion by means of the fastening screw in FIG. 2 has been effected, with the result that said parts e–j have come into cooperation with the inner surface 12a of the bridge sleeve 12 via their outer surfaces, the outer surface of a part e having been indicated by e'. The bearing force can be arranged with relatively high values, and tests have shown that it is possible to achieve bearing pressures of not less than ca. 250 Newton, which must be compared to the fact that the combined bite force of the whole bite is ca. 85 Newton. The gap a according to the view D is thus eliminated in the view E.

In a preferred embodiment, the outer surface 10b' of the respective portion 10b extends substantially parallel to the recessed wall 12a. The gaps between the various parts of the portion b are preferably zero in the unexpanded position.

The invention is not limited to the embodiment described above by way of example, and instead it can be modified within the scope of the attached patent claims and the inventive concept.

The invention claimed is:

1. An arrangement with an implant and attachment part, in which the attachment part comprises a recessed wall and the implant includes or cooperates with a substantially cylinder-shaped portion on a spacer sleeve applied to the implant, said substantially cylinder-shaped portion constituting front parts of a spacer arranged at or on upper parts of the implant, said attachment part and said recessed wall being arranged with displaceability in a main longitudinal direction of the implant relative to an outer surface of the substantially cylinder-shaped portion, said substantially cylinder-shaped portion being expandable so that, in a given position of longitudinal displacement, it is possible to achieve interaction between the outer surface of the substantially cylinder-shaped portion and the recessed wall and thus anchoring of the attachment part to the substantially cylinder-shaped portion, wherein:

the substantially cylinder-shaped portion comprises parts extending adjacent to one another which, during expansion, can be pressed outward in a radial direction;

the parts extending adjacent to one another are arranged with internal surfaces which combine to form an internal inner surface;

the parts extending adjacent to one another are expandable by means of a fastening screw which is provided with an outer screw surface which can cooperate with said internal inner surface, said parts extending adjacent to one another being expanded radially as a function of a position of insertion of the screw in the implant; and the parts extending adjacent to one another have lengths which substantially correspond to or are slightly smaller than a total length of the spacer sleeve.

2. The arrangement as claimed in claim 1, wherein the recessed wall is arranged in a bridge sleeve or directly in a bridge material.

3. The arrangement as claimed in claim 2, wherein the spacer sleeve is made of hard titanium and wherein the bridge sleeve is made of soft titanium.

4. The arrangement as claimed in claim 1, wherein both the recessed wall and the outer surface of the substantially cylinder-shaped portion are substantially cylindrical.

5. The arrangement as claimed in claim 1, wherein the parts extending adjacent to one another project into a recess with the recessed wall by at least $2/3$ of their lengths.

6. The arrangement as claimed in claim 1, wherein the fastening screw is made of gold, wherein the outer screw surface is designed as a truncated cone and is located at a head of the screw, and wherein the outer screw surface is arranged with a half cone angle of ca. 40°.

7. The arrangement as claimed in claim 1, wherein the outer surface of the substantially cylinder-shaped portion is designed with irregularities, by means of which the outer surface(s) cooperate.

8. The arrangement as claimed in claim 1, wherein the parts arranged adjacent to one another are arranged, during expansion, to work with movements of the order of $2/10$ to $4/10$ mm, for the purpose of preventing deformation or movements in the material of the parts extending adjacent to one another which exceed the modulus of elasticity of the material of the parts extending adjacent to one another.

9. The arrangement of claim 1, wherein the arrangement is a dental bridge.

10. The arrangement of claim 1, wherein the spacer sleeve extends substantially parallel to the recessed wall.

11. The arrangement of claim 7, wherein the irregularities comprise spikes.

12. An arrangement with an implant and attachment part, in which the attachment part comprises a recessed wall and the implant includes or cooperates with a substantially cylinder-shaped portion on a spacer sleeve applied to the implant, said attachment part and said recessed wail being arranged with displaceability in a main longitudinal direction of the implant relative to an outer surface of the substantially cylinder-shaped portion, said substantially cylinder-shaped portion being expandable so that, in a given position of longitudinal displacement, it is possible to achieve interaction between the outer surface of the substantially cylinder-shaped portion and the recessed wall and thus anchoring of the attachment part to the substantially cylinder-shaped portion, wherein:

the substantially cylinder-shaped portion comprises parts extending adjacent to one another and which, during expansion, can be pressed outward in a radial direction;

the parts extending adjacent to one another are arranged with internal surfaces which combine to form an internal inner surface;

the parts extending adjacent to one another are expandable by means of a fastening screw which is provided with an outer screw surface which can cooperate with said internal inner surface, said parts extending adjacent to one another being expanded radially as a function of a position of insertion of the screw in the implant; and the parts extending adjacent to one another are arranged, during expansion, to work with movements of ca. $3/10$ mm for the purpose of preventing deformation or movements in the material of the parts extending adjacent to one another which exceed a modulus of elasticity of the material of the parts extending adjacent to one another.

* * * * *